(12) United States Patent
De Haan et al.

(10) Patent No.: US 10,071,948 B2
(45) Date of Patent: Sep. 11, 2018

(54) ACID/SALT SEPARATION

(71) Applicant: PURAC BIOCHEM B.V., Gorinchem (NL)

(72) Inventors: André Banier De Haan, Best (NL); Jan Van Breugel, Woudrichem (NL); Paulus Loduvicus Johannes Van Der Weide, Breda (NL); Peter Paul Jansen, Oss (NL); José Maria Vidal Lancis, Vilassar de Mar (ES); Agustín Cerdà Baró, Cerdanyola Valles (ES)

(73) Assignee: PURAC BIOCHEM B.V., Gorinchem (NL)

( * ) Notice: Subject to any disclaimer, the term of this patent is extended or adjusted under 35 U.S.C. 154(b) by 0 days.

(21) Appl. No.: 15/378,888

(22) Filed: Dec. 14, 2016

(65) Prior Publication Data

US 2017/0088501 A1    Mar. 30, 2017

Related U.S. Application Data

(62) Division of application No. 14/238,686, filed as application No. PCT/NL2012/050574 on Aug. 16, 2012, now Pat. No. 9,550,712.

(60) Provisional application No. 61/524,353, filed on Aug. 17, 2011.

(30) Foreign Application Priority Data

Aug. 16, 2011    (EP) ..................................... 11177633

(51) Int. Cl.
| | | |
|---|---|---|
| *C07C 51/43* | (2006.01) | |
| *C01F 5/10* | (2006.01) | |
| *C01F 5/16* | (2006.01) | |
| *C01F 5/30* | (2006.01) | |
| *C01B 7/03* | (2006.01) | |

(52) U.S. Cl.
CPC .............. *C07C 51/43* (2013.01); *C01B 7/035* (2013.01); *C01F 5/10* (2013.01); *C01F 5/16* (2013.01); *C01F 5/30* (2013.01)

(58) Field of Classification Search
CPC . C07C 51/43; C01B 7/035; C01F 5/30; C01F 5/10; C01F 5/16
See application file for complete search history.

(56) References Cited

U.S. PATENT DOCUMENTS

| | | | |
|---|---|---|---|
| 5,304,676 | A | 4/1994 | Hindmarsh et al. |
| 6,660,505 | B2 | 12/2003 | Staley |
| 8,829,237 | B2 | 9/2014 | Hanchar et al. |
| 9,090,548 | B2 | 7/2015 | Cerda Baro et al. |
| 2006/0276674 | A1 | 12/2006 | Kushiku et al. |
| 2008/0223519 | A1 | 9/2008 | Locko et al. |
| 2010/0323416 | A1 | 12/2010 | Guettler et al. |
| 2014/0364632 | A1 | 12/2014 | De Haan et al. |

FOREIGN PATENT DOCUMENTS

| | | | |
|---|---|---|---|
| CN | 1427813 | A | 7/2003 |
| CN | 101748161 | A | 6/2010 |
| GB | 793700 | A * | 3/1958 |
| GB | 793700 | A | 4/1958 |
| JP | 2014-514263 | A | 6/2014 |
| JP | 2014-524254 | A | 9/2014 |
| JP | 2014-529595 | A | 11/2014 |
| JP | 2014-531408 | A | 11/2014 |
| KR | 2010-0122773 | A | 11/2010 |
| KR | 10-1051582 | * | 7/2011 |
| WO | 00/17378 | A2 | 3/2000 |
| WO | 01/030699 | A1 | 5/2001 |
| WO | 01/66508 | A2 | 9/2001 |
| WO | 2012/119064 | A1 | 9/2012 |
| WO | 2013/025105 | A1 | 2/2013 |
| WO | 2013/025106 | A1 | 2/2013 |

OTHER PUBLICATIONS

Shand, Mark A. The chemistry and technology of magnesia. John Wiley & Sons, 2006; excerpt p. 1-3.*
Davies, M.,"The solubilities of dicarboxylic acids in benzene and aqueous solutions." Transactions of the Faraday Society 49 (1953): 1405-1410.*
KR 10-1051582—English Translation USPTO Mar. 2015 p. 1-55.*
Jun. 21, 2017 Office Action issued in U.S. Appl. No. 15/378,830.
Mar. 11, 2016 Office Action issued in Chinese Patent Application No. 201280039672.2.
Mar. 1, 2016 Office Action issued in Japanese Patent Application No. 2014-525959.
Mar. 1, 2016 Office Action issued in Japanese Patent Application No. 2014-525960.
Apr. 21, 2016 Office Action issued in Eurasian Patent Application No. 201490410.
Apr. 21, 2016 Office Action issued in Eurasian Patent Application No. 201490355.
Apr. 27, 2016 Office Action issued in Ukrainian Patent Application No. 2014 02002.
Feb. 5, 2016 Office Action issued in Chinese Patent Application No. 201280045958.1.
Feb. 6, 2016 Office Action issued in Chinese Patent Application No. 201280046341.1.
Jan. 20, 2016 Office Action issued in Ukrainian Patent Application No. A 2014 02002.

(Continued)

*Primary Examiner* — John M Mauro
(74) *Attorney, Agent, or Firm* — Oliff PLC

(57) ABSTRACT

The invention provides a method for preparing a carboxylic acid, which method includes the steps of providing magnesium carboxylate, wherein the carboxylic acid corresponding with the carboxylate has a solubility in water at 20° C. of 80 g/100 g water or less; acidifying the magnesium carboxylate with HCl, thereby obtaining a solution comprising carboxylic acid and magnesium chloride ($MgCl_2$); optionally a concentration step, wherein the solution comprising carboxylic acid and $MgCl_2$ is concentrated; precipitating the carboxylic acid from the solution comprising the carboxylic acid and $MgCl_2$, thereby obtaining a carboxylic acid precipitate and a $MgCl_2$ solution.

30 Claims, No Drawings

(56) References Cited

OTHER PUBLICATIONS

Haynes, W. M. "Aqueous Solubility and Henry's Law Constants of organic Compounds." CRC Handbook of Chemistry and Physics 96 (2011), p. 5-164-5-185.
Kramer, H.J.M., Encyclopedia of Separation Science, 2000, Elsevier Science Ltd., Ed. I. D. Wilson, Crystallization p. 64-84.
Jul. 14, 2015 Office Action issued in U.S. Appl. No. 14/238,666.
May 29, 2013 International Search Report issued in International Patent Application No. PCT/EP2013/052525.
May 29, 2013 Written Opinion issued in International Patent Application No. PCT/EP2013/052525.
KR 10-2010-012273 English Machine Translation EPO accessed Feb. 17, 2015. p. 1-48.
Davies, M., "The solubilities of dicarboxylic acids in benzene and aqueous solutions." Trans. Faraday Soc. 49 (1953): 1405-1410.
Shand, M. A., The chemistry and technology of magnesia. John Wiley & Sons (2000), exerpt, p. 1-3.
Dec. 22, 2014 Office Action issued in U.S. Appl. No. 14/238,633.
Bischoff, J.L. et al., "The generation of HCl in the system CaCl2—H2O: Vapor liquid relations from 380-500° C.," Geochimica et Cosmochimica Acta, 1996, pp. 7-16, vol. 60, No. 1.
Nov. 13, 2012 International Search Report issued in International Application No. PCT/NL2012/050572.
Nov. 13, 2012 Written Opinion issued of the International Searching Authority issued in International Application No. PCT/NL2012/050572.
U.S. Appl. No. 14/238,666 in the name of André Bainer De Haan et al. filed Mar. 12, 2014.
U.S. Appl. No. 14/238,633 in the name of André Bainer De Haan et al. filed Feb. 12, 2014.
Nov. 13, 2012 International Search Report issued in International Application No. PCT/NL2012/050573.
Nov. 13, 2012 Written Opinion of the International Searching Authority issued in International Application No. PCT/NL2012/050573.
International Search Report issued in International Application No. PCT/NL2012/050574 dated Nov. 13, 2012.
Written Opinion of the International Seaching Authority Report issued in International Application No. PCT/NL2012/050574 dated Nov. 13, 2012.
Mar. 15, 2017 Office Action Issued in Chinese Patent Office Application No. 201280045958.1.
Mar. 23, 2017 Office Action Issued in Chinese Patent Office Application No. 201280046341.1.
Oct. 27, 2017 Office Action issued in Chinese Patent Application No. 201280039672.2.

* cited by examiner

ACID/SALT SEPARATION

This is a Division of application Ser. No. 14/238,686 filed Jul. 28, 2014, which in turn is a National Stage application of PCT/NL2012/050574 filed Aug. 16, 2012, which claims the benefit of U.S. Provisional Application No. 61/524,353 filed Aug. 17, 2011 and European Patent Application No. 11177633.2 filed Aug. 16, 2011. The disclosure of the prior applications is hereby incorporated by reference herein in its entirety.

The invention is directed to a method for preparing a carboxylic acid. The production of carboxylic acids leads to various unwanted byproducts, especially when produced by means of fermentation. Fermentation processes wherein carboxylic acids are excreted by the micro-organisms will result in a decrease in the pH. Since such a decrease in pH can damage the micro-organism's metabolic process, it is common practice to add a base in the fermentation media in order to neutralize the pH. As a result, carboxylic acid produced in the fermentation media is typically present in the form of a carboxylic acid salt.

A disadvantage of obtaining the carboxylic acid from a fermentation process in the form of a carboxylic acid salt is that one or more additional steps are required to separate the carboxylic acid from the salt, i.e. convert the salt to a carboxylic acid, which typically leads to loss of carboxylic acid and/or carboxylic acid salts and thus to a decrease in the total fermentation or process yield.

A further disadvantage of such steps is that these typically lead to considerable salt waste. For example, the separation steps often comprise acidulation of the carboxylic acid salt using sulphuric acid, resulting in a sulphate salt as a waste product.

An object of the invention is to provide a separation step in which the carboxylic acid is separated from a salt solution with a suitable conversion yield.

A further object of the invention is to provide a method with no or substantially no salt waste.

The present invention also provides a very robust method which is capable of separating the targeted carboxylic acid from salt solutions with of significant low quality due to the presence At least one of these objects was met by providing a method for preparing a carboxylic acid, which method comprises the steps of providing magnesium carboxylate, wherein the carboxylic acid corresponding with the carboxylate has a solubility in water at 20° C. of 80 g/100 g water or less, acidifying the magnesium carboxylate with hydrogen chloride (HCl), e.g. hydrochloric acid, thereby obtaining a solution comprising carboxylic acid and magnesium chloride ($MgCl_2$);

optionally a concentration step, wherein the solution comprising carboxylic acid and $MgCl_2$ is concentrated;

precipitating the carboxylic acid from the solution comprising the carboxylic acid and $MgCl_2$, thereby obtaining a carboxylic acid precipitate and a $MgCl_2$ solution.

The inventors found that the addition of HCl to a magnesium salt of the selected carboxylic acids and subsequent precipitation of the carboxylic acid from the solution leads to a very efficient isolation of the carboxylic acid from said magnesium carboxylate solution.

In particular, it was found that carboxylic acid could be precipitated from a carboxylate solution acidified with HCl with a very high efficiency. Without wishing to be bound by any theory, the inventors expect that the high efficiency of the precipitation is due to a particular high salting out effect of $MgCl_2$ in the solution. In particular, the salting out effect is expected to be caused by the specific combination of HCl, magnesium and carboxylic acid. Since salting out effects are generally hard to predict, the particular high salting out effect for these acids observed in the method of the invention came as a surprise to the inventors.

Thus, using the method of the invention, a carboxylic acid precipitate can be obtained in a high yield from a magnesium carboxylate solution, which solution is for example a fermentation mixture obtained in a fermentation process. Furthermore, the obtained carboxylic acid precipitate has a relatively high purity, since the precipitation step in the method of the invention does not result in precipitation of large amounts of compounds other than carboxylic acid. Furthermore, a magnesium chloride solution is obtained. This solution can be processed further as described below.

Furthermore, the specific choice for HCl and magnesium carboxylate provides for a reduction in salt waste, in particular when combined with a thermal decomposition step.

Preferably, the method further comprises the steps of subjecting the $MgCl_2$ solution to a thermal decomposition step at temperatures of at least 300° C., thereby decomposing the $MgCl_2$ to magnesium oxide (MgO) and HCl; and optionally dissolving the HCl formed in the thermal decomposition step in water, thereby obtaining a HCl solution; and optionally bringing the MgO in contact with water, thereby obtaining $Mg(OH)_2$, which $Mg(OH)_2$ solution is optionally recycled for use in a fermentation process, preferably the fermentation process with which the magnesium carboxylate from the first step is provided.

The advantage of these additional steps is that a method may be obtained that has no or substantially no salt waste. The HCl solution may be recycled to the acidulation step of the method of the invention. The $Mg(OH)_2$ can be recycled for use in the fermentation process.

The term "carboxylate" as used herein refers to the conjugate base of a carboxylic acid, which generally can be represented by the formula RCOO—. The term "magnesium carboxylate" refers to the magnesium salt of the carboxylic acid to be prepared in the method of the invention.

The term "carboxylic acid corresponding with the carboxylate" refers to the carboxylic acid that can be obtained by acidifying the carboxylate. This is also the carboxylic acid that is the product the method of the invention. It may therefore also be referred to as acidified carboxylate. The carboxylic acid corresponding with the carboxylate can generally be represented by the formula RCOOH.

The term "precipitating" as used herein refers to the formation of solid material starting from a fully dissolved state. Carboxylic acid can be precipitated in crystalline form or in amorphous form. By precipitating carboxylic acid according to the method of the invention, the carboxylic acid may also be purified. In case the magnesium carboxylate solution comprises dissolved impurities, precipitation of carboxylic acid typically separates the carboxylic acid from such impurities.

The term "solution to be precipitated" as used herein refers to the solution that is to be subjected to precipitation. Typically, this term refers to the solution comprising carboxylic acid and $MgCl_2$ obtained after acidulation, optionally after this solution has been subjected to a concentration step and/or a step wherein extra $MgCl_2$ is added. However, in case of a second or further precipitation step, the term "solution to be precipitated" refers to the $MgCl_2$ solution obtained after the final or latest precipitation step, optionally after this solution has been subjected to a concentration step and/or a step wherein extra $MgCl_2$ is added. Such $MgCl_2$ solutions may still comprise carboxylic acid, which may be obtained by subjecting it to a second or further precipitation step.

Any magnesium carboxylate can be used, which in acidified form (i.e. wherein the corresponding carboxylic acid) has a solubility in water close to or lower than $MgCl_2$. Consequently, the carboxylic acid to be precipitated in the method of the invention has a solubility in water of 80 g/100 g water or less at 20° C. Carboxylic acids having a solubility in water considerably higher than $MgCl_2$ are not suitable to be precipitated with the method of the invention, because in this case large amounts of $MgCl_2$ will precipitate when precipitating the carboxylic acid, such that no suitable separation is obtained.

Preferably, the carboxylic acid corresponding with the carboxylate has a solubility that is lower than that of $MgCl_2$, as measured in water at 20° C., i.e. has a solubility in water of less than 54.5 g/100 g water at 20° C. (anhydrate). More preferably, the carboxylic acid has a solubility that is considerably lower than $MgCl_2$, such that $MgCl_2$ does not precipitate together with the carboxylic acid from the solution in the precipitation step. Therefore, the carboxylic acid preferably has a solubility in water at 20° C. of less than 60 g/100 water, more preferably less than 50 g/100 g water, even more preferably less than 40 g/100 g water, even more preferably less than 30 g/100 g water, even more preferably less than 10 g/100 g water, even more preferably less than 7 g/100 g water. The lower boundary for the solubility of the carboxyic acid is not critical.

The carboxylic acid to be prepared by the method of the invention may be selected from the group consisting of succinic acid, adipic acid, itaconic acid, 2,5-furandicarboxylic acid, fumaric acid, citric acid, maleic acid, glutaric acid, malonic acid, oxalic acid and fatty acids having more than 10 carbon atoms. Good results have been obtained using a carboxylic acid selected from the group consisting of adipic acid, itaconic acid, 2,5-furandicarboxylic acid and fumaric acid. In one embodiment, the carboxylic acid is not succinic acid.

The magnesium carboxylate used in the invention may be selected from the magnesium salts of the above-mentioned groups of carboxylic acids.

The magnesium carboxylate may be provided in solid (e.g. crystalline) form. Alternatively, the magnesium carboxylate may be in dissolved form, for example as part of a solution or suspension. Such a solution or suspension comprising dissolved magnesium carboxylate may be aqueous and may in particular be obtained in a fermentation process. An example of a suspension may for example be a suspension comprising dissolved magnesium carboxylate and insoluble biomass, such as a fermentation broth. In case the magnesium carboxylate is provided in dissolved form, the magnesium carboxylate solution or suspension may have a concentration of 1-700 g, preferably 100-600 g, more preferably 200-500 g magnesium carboxylate per liter solution or suspension.

In case the carboxylate is provided as a solution or suspension, the magnesium carboxylate concentration at which carboxylic acid precipitation occurs upon acidulation may depend on the HCl concentration. For example, when using a HCl solution with a high HCl concentration (e.g. between 20 and 30 wt. %) to acidify the carboxylate, precipitation of carboxylic acid may occur at relatively low carboxylate concentrations (e.g. at around or between 1 and 10 wt. %). However, when using lower HCl concentration (e.g. between 10 and 20 wt. %), higher carboxylate concentration (e.g. between 10 and 50 wt. %) may be required for precipitation to occur. For practical reasons, the upper limit of the magnesium carboxylate concentration in a magnesium carboxylate solution or suspension is the maximum solubility of magnesium carboxylate at a maximal temperature of 75 degrees Celsius. This concentration is typically around 20 wt. % magnesium carboxylate or less, based on the total weight of the solution or suspension. However, it may vary for the specific carboxylate used. Concentrations higher than 20 wt. % may require the solution to have a temperature of 75° C. or above in order to have the magnesium carboxylate in completely dissolved form, which temperature is bad for the equipment with regards to the corrosion sensitivities of the materials used in the presence of HCl.

To yield as much carboxylic acid as possible after acidulation and precipitation, the carboxylate concentration going into the acidulation is preferably as high as possible. In case the magnesium carboxylate is provided as a solution, the upper limit of the magnesium carboxylate concentration is determined by the solubility of the magnesium carboxylate and the temperature at which the equipment is still sufficiently resistant against corrosion due to HCl. In case the carboxylate is provided as a suspension, the stirrability of the suspension typically determine the upper limit. In case the carboxylate is provided as a solid cake, the solid liquid separation and resulting adhering water typically determine the upper limit. To support a high carboxylic acid yield after acidulation and precipitation, the HCl concentration is preferably as high as economically feasible, as introduction of extra water will dilute the system. The combination of the above mentioned input concentrations of carboxylate and HCl must favorably result in a situation where $MgCl_2$ remains in solution and as much carboxylic acid as possible precipitates during the precipitation step. The skilled person will be able to vary the two concentrations to obtain the desired result. For example, good results have been obtained using a combination of 15-25 wt. % HCl and a magnesium carboxylate concentration of 20-50 wt. %.

In case a magnesium carboxylate solution or suspension is obtained from a fermentation process which does not have a sufficiently high magnesium carboxylate concentration, the solution may be concentrated, for example by evaporation.

In a preferred embodiment of the present invention, the magnesium carboxylate is obtained in a fermentation which uses a magnesium-based base for neutralisation in order to directly produce magnesium carboxylate—in contrast to first conducting fermentation and then adding a base to form magnesium carboxylate- to keep the process as simple as possible and to prevent using additional processing steps.

The above-mentioned magnesium-based fermentation may also be run at conditions so that the resulting fermentation product is a mixture of carboxylic acid acid and magnesium carboxylate which will lead to less carboxylate to be acidulated and precipitated.

The method of the invention further comprises an acidulation step, wherein the magnesium carboxylate is acidified with HCl, thereby obtaining a solution comprising carboxylic acid and $MgCl_2$. The inventors found that HCl is preferred as an acidifying agent over other acids, such as $H_2SO_4$. First, the use of HCl provides for an efficient precipitation, such as the advantageous salting out effect described above. In particular, the presence of $MgCl_2$ decreases the solubility of the carboxylic acid, which results in a more efficient precipitation of the acid. Furthermore, the reaction of magnesium carboxylate with HCl results in salt with a relatively high solubility ($MgCl_2$), in particular compared to other magnesium salts including $MgSO_4$ and also compared to many carboxylic acids. A high solubility of the salt obtained by acidifying is desirable, because as little of this salt as possible should precipitate in the precipitation step. The maximum concentration of carboxylic acid in the solution to be precipitated is therefore in part determined by the solubility of the salt obtained in the acidulation step. Thus, in case the salt has a high solubility, a high carboxylic acid concentration can be obtained without precipitation of the salt, which results in an efficient precipitation of the carboxylic acid.

Acidulation is typically conducted using an excess of HCl. The excess is preferably small, such that the $MgCl_2$ solution obtained after precipitation is not highly acidic, which may not be desirable in view of further processing such a solution. For example, the excess of HCl used may be such that the resulting $MgCl_2$ solution after precipitation has a pH of 1 or higher, such as a pH of about 1.5. The skilled person knows how to calculate based on reaction stochiometrics the maximal allowable excess for such a pH of 1 or higher. To obtain a sufficiently complete acidulation, the resulting $MgCl_2$ solution preferably has a pH below 4, more preferably below 3.

HCl acidulation may for example be conducted by bringing the magnesium carboxylate in contact with HCl, for example by bringing the magnesium carboxylate (in solid form, suspension or solution) in contact with an aqueous HCl solution or by bringing a magnesium carboxylate solution or suspension in contact with HCl gas.

If a HCl solution is used in the acidulation step, it preferably comprises at least 5 wt. %, more preferably at least 10 wt. % and even more preferably at least 20 wt. % HCl. Such concentrations are generally sufficient to acidify the magnesium carboxylate. High HCl concentrations may be desirable due to the above-mentioned salt out effect. Due to the low boiling point of HCl and the $HCl/H_2O$ azeotrope, the HCl concentration in a HCl solution will typically not be higher than 40%, in particular when using a HCl solution at atmospheric pressure. Preferably, a HCl concentration is used with a concentration of 15-25 wt. % HCl, based on the total weight of the HCl solution. Nevertheless, HCl concentrations of up to 100% may also be employed, in which case a HCl solution is typically used under increased pressure (e.g. above atmospheric pressure) and/or low temperatures (e.g. below 20° C.).

In case HCl gas is used, HCl gas may be contacted by bringing it in contact with a carboxylate solution or suspension. In particular, HCl gas may be blown through the solution or suspension. In case HCl gas is used, the HCl may originate from a thermal decomposition step, such as for example described below.

Preferably, acidification is conducted at a temperature of 75° C. or less. At higher temperatures, it becomes uneconomical to adapt equipment to the harsh conditions. In view of the freezing point of water, acidification is typically conducted at a temperature above 0° C. Temperatures above 20° C. may be preferred to avoid the use of cooling machines. Temperatures of 40° C. or more, or even 60° C. or more are even more preferred, because more magnesium carboxylate can be dissolved at these higher temperatures. The temperature of the magnesium carboxylate solution or suspension is typically determined by and corresponds with the temperature at which the acidification is conducted.

The method of the invention may comprise a concentration step, wherein the solution obtained after acidulation with HCl is concentrated. A higher concentration of carboxylic acid in the solution will increase the efficiency of the carboxylic acid precipitation. The concentration step may be conducted by evaporation. In the concentration step, 10-90% of the total amount of water present in the solution may be removed. However, preferably no $MgCl_2$ is precipitated as a result of the concentration. Therefore, the solution obtained after acidulation is preferably concentrated to a $MgCl_2$ concentration that is equal or lower to the saturation point of $MgCl_2$.

The method of the invention further comprises precipitating the carboxylic acid from the solution obtained in the acidulation step or, if present, from the solution obtained in the concentration step. This step may be referred to as the (first) precipitation step. Precipitation may be conducted by any precipitation method known in the art, such as reactive precipitation or by cooling, concentrating, evaporating the solution to be precipitated or by adding an antisolvent to the solution to be precipitated.

Precipitation is preferably established by acidifying the magnesium carboxylate with HCl. This type of precipitation may be referred to as reactive precipitation. In reactive precipitation, precipitation takes place during acidulation. Consequently, acidifying the magnesium carboxylate and precipitating the thus obtained carboxylic acid are conducted as one step. Accordingly, the method of the invention will comprise the steps of providing magnesium carboxylate obtained optionally in a fermentation process (as described above); and acidifying the magnesium carboxylate with HCl (e.g. an aqueous HCl solution), thereby obtaining a carboxylic acid precipitate and a $MgCl_2$ solution. It is noted that the precipitation step actually results in a suspension with the carboxylic acid precipitate present in the $MgCl_2$ solution.

Reactive precipitation can be conducted by choosing the conditions in the acidulation step such that immediate precipitation of the carboxylic acid can occur. The skilled person will know how to establish such conditions. In particular, the magnesium carboxylate concentration may be chosen such that the acidulation with HCl will result in a carboxylic acid concentration that is higher than the saturation point of the carboxylic acid. The exact concentration of the carboxylic acid at its saturation point will vary for the carboxylic acid used.

The precipitation step may also be conducted by cooling the solution to be precipitated, e.g. the solution formed in the acidulation step, or, if present, the solution obtained in the concentration step. This type of precipitation may be referred to as cooling precipitation. The cooling step may require that the solution to be precipitated is first heated to a temperature at which substantially all $MgCl_2$ and carboxylic acid are dissolved. The solution to be precipitated may be cooled from a temperature above the nucleation temperature of the carboxylic acid in the solution to a temperature below the nucleation temperature of the carboxylic acid in the solution. The nucleation temperature is the highest temperature at which solids, in particular, precipitate, is formed. This temperature is i.a. dependent on the concentration of $MgCl_2$, carboxylic acid and the presence of other components. Therefore, it is not possible to give a single temperature value for the nucleation temperature. However, in general, the solution to be precipitated is cooled from a temperature of at least 35° C. to a temperature of less than 30° C., preferably at least 40° C. to a temperature of less than 25° C. Higher temperature differences make it possible to increase the yield of carboxylic acid precipitate. In case of a cooling precipitation the carboxylic acid concentration prior to cooling is preferably as close to the solubility as is economically feasible. The carboxylic acid concentration may be equal or up to 5, preferably up to 10 g/L lower than the saturation point of the carboxylic acid.

Furthermore, precipitation may be established by concentrating the solution comprising the carboxylic acid and $MgCl_2$, preferably by evaporation. Evaporation of part of the solvent of the solution comprising the carboxylic acid and $MgCl_2$ will result in a higher concentration of the carboxylic acid and a stronger salting out effect, which enhances precipitation.

Furthermore, precipitation may be established by adding an antisolvent to the solution to be precipitated. Examples of antisolvents are alcohols, ethers and ketones.

Preferably, the $MgCl_2$ solution obtained after precipitation may be subjected to a second and/or further precipitation step, thereby forming additional carboxylic acid precipitate and a second and/or further $MgCl_2$ solution. The second or further precipitation step may be conducted to recover at least part of the carboxylic acid remaining in the $MgCl_2$ solution obtained in the previous precipitation step. In this case, this previous precipitation step of the invention may be referred to as the first precipitation step. The $MgCl_2$ solution obtained in the first precipitation of the method may still comprise small amounts of carboxylic acid. To recover at least part of this carboxylic acid, a second precipitation step may be conducted. Such a second precipitation step may be conducted under similar conditions as the first precipitation step, including a concentration step and/or the addition of $MgCl_2$ conducted prior to the precipitation step.

In a preferred embodiment, the method of the invention comprises a first precipitation reaction, which is a reactive precipitation step, after which the $MgCl_2$ solution obtained in this step is subjected to a cooling and/or evaporation step. The cooling and/or evaporation step are further precipitation steps, wherein additional carboxylic acid is precipitated and carboxylic acid losses and process yields are thus improved.

Prior to any precipitation step, magnesium chloride may be added to the solution to be precipitated or to the HCl solution. This solution to be precipitated may be the solution comprising the magnesium carboxylate solution (e.g. in case of reactive precipitation) or the solution comprising carboxylic acid and magnesium chloride (as obtained in the acidulation step). Such added magnesium chloride may increase the salting out effect, thereby enhancing the precipitation of carboxylic acid.

Preferably, the method further comprises the steps of
subjecting the $MgCl_2$ solution to a thermal decomposition step at temperatures of at least 300° C., thereby decomposing the $MgCl_2$ to MgO and HCl; and
dissolving the HCl formed in the thermal decomposition step in water, thereby obtaining a HCl solution; and
bringing the MgO in contact with water, thereby obtaining $Mg(OH)_2$.

As described above, the advantage of these additional steps is that a method may be obtained that has no or substantially no salt waste.

Thermal decomposition of chlorides is commonly known from the steel industry, wherein iron(III)chloride ($FeCl_3$) is thermally decomposed into iron(II)chloride ($FeCl_2$) and chlorine gas ($Cl_2$). In this field, thermal decomposition of $MgCl_2$ to HCl and MgO is also known, for example from GB 793,700. Thermal decomposition as described herein may also be suitably applied in the method of the invention. Accordingly, thermal decomposition used in the invention may be conducted by spraying the $MgCl_2$ solution into contact with a stream of hot gas. The temperature of the hot gas is equal to the temperature at which thermal decomposition is conducted, as described below.

The combination of thermal decomposition in an acid/salt separation of magnesium carboxylate from a fermentation process has to the applicant's knowledge not been described earlier. The inventors realised that $MgCl_2$ can be thermally decomposed by pyrohydrolysis at relative low temperatures (for example in contrast to $CaCl_2$, which starts to decompose at about 800° C. or higher). This is advantageous, because the MgO formed will still have a sufficiently high reactivity that it can be effectively used in for example fermentation.

Suitable apparatuses for conducting thermal decomposition are known in the art. Thermal decomposition may be conducted using a roaster, for example a spray roaster or a fluid bed roaster. Such apparatuses can for example be obtained at SMS Siemag. The use of a spray roaster is preferred. A spray roaster has low energy costs (also compared to a fluid bed roaster), because it requires relatively temperatures (as described below). A spray roaster further produces reactive MgO particles, which are very suitable for use as a neutralizing agent in fermentation.

Preferably, thermal decomposition is conducted at a temperature of a least 300° C., which is the minimum temperature at which $MgCl_2$ decomposes. Preferably, thermal decomposition is conducted at a temperature of at least 350° C., for example 350-450° C. Due to energy costs, the temperature is preferably below 1000° C., more preferably below 800° C. For example, the temperature at which thermal decomposition is conducted may be 350-600° C. or 300-400° C. In addition, using a too high temperature for the thermal decomposition step is undesirable, because it will reduce the reactivity of the MgO formed, such that it is less suitable for use as a neutralizing agent in fermentation.

Thermal decomposition as applied in the method of the invention is preferably conducted at a pressure of 0.1-10 bar. However, the use of elevated pressure may be undesirable, because of an increased risk of corrosion due to the HCl not being able to condense. Preferably, thermal decomposition is conducted at atmospheric pressure, in particular when using a roaster, to avoid unnecessary energy costs and the need for expensive high pressure equipment.

Magnesium oxide (MgO) is one of the products of the thermal decomposition and is typically obtained in the form of a powder. The magnesium oxide is hydrated with water, e.g. by quenching the MgO with water, thereby forming a magnesium hydroxide ($Mg(OH)_2$) suspension. The magnesium hydroxide suspension is preferably recycled for use in the fermentation process. For example, the $Mg(OH)_2$ may be used as a neutralizing agent in a fermentation process. In this case, the $Mg(OH)_2$ may first be washed with water to remove chloride ions, typically to a content less than 1000 ppm. The presence of chloride ions is undesirable, because they may cause corrosion problems when added to a fermentation vessel. Since $Mg(OH)_2$ has a low solubility in water, such a washing step will typically not result in the loss of significant amounts of $Mg(OH)_2$. Alternatively, the $Mg(OH)_2$ is first converted to magnesium carbonate ($MgCO_3$), which is then used as a neutralizing agent in a fermentation process. A combination of these two steps may also be applied in which part of the $Mg(OH)_2$ is washed and re-used and a second part is converted into $MgCO_3$ and then re-used in the process. Part of the MgO may even be directly used in the fermentation.

The HCl obtained in the thermal decomposition step may be dissolved in water, thereby forming an aqueous HCl solution. Preferably, the HCl obtained in the thermal decomposition step is recycled by using it in the acidification step in the method of the invention, for example as HCl gas or as an aqueous HCl solution.

The magnesium carboxylate provided in the method of the invention may be obtained in a fermentation process. In such a fermentation process a carbohydrate source is typically fermented by means of a micro-organism to form a carboxylic acid. Subsequently, a magnesium base is added as neutralising agent during fermentation to provide the magnesium salt of the carboxylic acid. Examples of suitable magnesium bases are magnesium hydroxide ($Mg(OH)_2$), magnesium carbonate ($MgCO_3$) and magnesium bicarbonate ($Mg(HCO_3)_2$). The advantage of the use of $Mg(OH)_2$ as a base is that this compound can be provided by the method of the invention. The use of $MgCO_3$ may also desirable and can be easily obtained by converting $Mg(OH)_2$ obtained in the method of the invention. Furthermore, the use of $MgCO_3$ or $Mg(OH)_2$ is desirable, because hydroxide and carbonate are not expected to have a negative effect on the salting out effect of the method of the invention (any carbonate left after neutralising may leave the solution as gaseous $CO_2$).

The fermentation process may comprise a purification step, wherein the magnesium carboxylate obtained during or after crystallisation is crystallised from the fermentation broth, which may then be subsequently dissolved in water to form an aqueous solution, which typically has a higher concentration of carboxylate than the fermentation broth. Such a purification step may have the advantage that a higher yield can be obtained in the first precipitation step due to the higher concentration of the magnesium carboxylate.

However, as described above, the magnesium carboxylate preferably remains in dissolved form when the magnesium base is added as a neutralizing agent. This has the advantage that the magnesium carboxylate is pump able and can be directly used in the acidulation step. Furthermore, the acidulation step is easy to control when the magnesium carboxylate is in dissolved form. In particular, the magnesium carboxylate present in the magnesium carboxylate solution or suspension obtained after adding the magnesium base comprises at least 95 wt. %, preferably at least 99 wt. % of magnesium carboxylate in dissolved form. Small amounts of solids (up to 10 wt. %) of solid matter may not yet lead to the negative effects described above.

The crystallisation may comprise at least one of a concentration step, such as a water evaporation step, a cooling step, a seeding step, a separation step, a washing step and a re-crystallisation step. Concentration may be performed as a separate step or together with crystallisation (e.g. evaporative-crystallisation).

The invention is further illustrated by the following examples.

EXAMPLE 1: MAGNESIUM DICARBOXYLATE PREPARATION

Magnesium hydroxide was added to a solution of dicarboxylic acid in water and heated up to complete dissolution. Four different carboxylic acids were used: adipic acid, fumaric acid, itaconic acid and 2,5-furandicarboxylic acid. The amounts of each component are given in Table 1. The resulting dicarboxylate solution was meant to resemble a magnesium dicarboxylate solution obtained in a fermentation process. Although a magnesium dicarboxylate solution obtained in a fermentation process generally comprises compounds other than magnesium dicarbooxylate, such as a relatively large amount of impurities, the magnesium dicarboxylate solution prepared for this example was considered to sufficiently resemble a magnesium dicarboxylate solution obtained in a fermentation process to show the proof of principle that the invention works.

TABLE 1

| Type of dicarboxylic acid | Magnesium oxide [g] | Dicarboxylic acid [g] | water [g] |
|---|---|---|---|
| Aclipic acid | 47 | 171 | 767 |
| Fumaric acid | 6.4 | 18.6 | 1082 |
| Itaconic acid | 51 | 164 | 745 |
| 2,5-furandicarboxylic acid | 2.4 | 9.5 | 528 |

EXAMPLE 2: DICARBOXYLIC ACID PRECIPITATION

A certain amount of an aqueous solution of HCl was added to the magnesium dicarboxylate solution from Example 1, as indicated in Table 2. The temperature of the thus obtained mixtures is also given in Table 2. The mixture was cooled to 20° C. and a precipitate was formed. During cooling, samples were taken of the solution for each 10±1 centigrade. The composition of the samples and the total amount of precipitate formed were determined.

TABLE 2

| Type of dicarboxylic acid | Magnesium Dicarboxylate solution [g] | HCl concentration [% (g/g)] | HCl [g] | T, o [° C.] |
|---|---|---|---|---|
| Aclipic acid | 985 | 37 | 231 | 80 |
| Fumaric acid | 1107 | 34.4 | 36 | 60 |
| Itaconic acid | 960 | 37 | 249 | 60 |
| 2,5-furandicarboxylic acid | 541 | 37 | 12 | 50 |

The samples were taken only from the solution (for sampling, stirrer was stopped some few seconds, and after crystal settling, sample taken from the upper layer). Magnesium and dicarboxylic acid in solution were analyzed and expressed as g/g water. The amount of crystal produced was calculated as difference between the initial dicarboxylic mass and the remaining dicarboxylic mass in solution.

The results are shown in Table 3-Table 6 for adipic acid, fumaric acid, itaconic acid and 2,5 furandicarboxylic acid respectively.

TABLE 3

| Temperature (° C.) | Aclipic Acid concentration in the solution (wt %) | Mg Concentration in the solution (wt %) | Amount of precipitate formed (g) |
|---|---|---|---|
| 81 | 14.2 | 2.7 | 0 |
| 70 | 11.5 | 2.6 | 37.1 |
| 60 | 6.1 | 2.7 | 104.9 |
| 51 | 3.5 | 2.8 | 134.8 |
| 40 | 2 | 2.7 | 151.3 |
| 30 | 1.2 | 2.8 | 160.0 |
| 20 | 0.7 | 2.8 | 165.3 |

TABLE 4

| Temperature (° C.) | Fumaric Acid concentration in the solution (wt %) | Mg concentration in the solution (mg/kg) | Amount of precipitate formed (g) |
|---|---|---|---|
| 60 | 1.6 | 3420 | 0 |
| 50 | 1.1 | 3450 | 5.8 |
| 39 | 0.7 | 3450 | 10.4 |

TABLE 4-continued

| Temperature (° C.) | Fumaric Acid concentration in the solution (wt %) | Mg concentration in the solution (mg/kg) | Amount of precipitate formed (g) |
|---|---|---|---|
| 30 | 0.5 | 3450 | 12.6 |
| 20 | 0.5 | 3470 | 12.6 |

TABLE 5

| Temperature (° C.) | Itaconic Acid concentration in the solution (wt %) | Mg concentration in the solution (% [g/g]) | Amount of precipitate formed (g) |
|---|---|---|---|
| 60 | 13.2 | 2.6 | 0 |
| 50 | 9.4 | 2.8 | 50.7 |
| 41 | 6.0 | 2.7 | 92.6 |
| 30 | 4.1 | 2.8 | 114.7 |
| 20 | 2.6 | 2.4 | 131.5 |

TABLE 6

| Temperature (° C.) | 2,5-Furandicarboxylic Acid concentration in the solution (%) | Mg Conc (wt %) | Amount of precipitate formed (g) |
|---|---|---|---|
| 84 | 0.52 | 3260 | 6.6 |
| 72 | 0.19 | 3350 | 8.4 |
| 62 | 0.38 | 3330 | 7.3 |
| 53 | 0.25 | 2930 | 8.0 |
| 42 | 0.33 | 3420 | 7.6 |
| 32 | 0.14 | 3340 | 8.6 |
| 22 | 0.06 | 1190 | 9.1 |

These findings correspond to a total recovery of over 97% for adipic acid, 72% for fumaric acid, 80% for itaconic acid and 96% for 2,5-furandicarboxylic acid.

This example shows that adipic acid, fumaric acid, itaconic acid and 2,5-furandicarboxylic acid can be efficiently obtained using the method of the invention. During precipitation, the majority of the dicarboxylic acid precipitates, while substantially all magnesium ions remain in solution. It can be concluded that acidulation with HCl and subsequent crystallization results in a very efficient separation of the dicarboxylic acids from the magnesium dicarboxylate solution.

EXAMPLE 3: PRECIPITATION OF CITRIC ACID

In a first experiment with citric acid, 5 g of citric acid was added to a saturated solution of $MgCl_2$.

In a second experiment with citric acid, 15 g of citric acid was added to a saturated solution of $MgCl_2$.

In a third experiment with citric acid, 5 g of magnesium chloride was added to a saturated solution of citric acid.

In a fourth experiment with citric acid, 15 g of magnesium chloride was added to a saturated solution of citric acid.

In all four experiments, a precipitate was formed. The citric acid and Mg content of the precipitate was analysed using HPLC. The results are shown in Table 7.

TABLE 7

| Experiment | citric acid (wt. %) | Mg (wt. %) | $MgCl_2$ (wt. %)* |
|---|---|---|---|
| 1 | 97.4 | 0.76 | 2.99 |
| 2 | 92.7 | 1.18 | 4.62 |
| 3 | 93.0 | 0.14 | 0.56 |
| 4 | 86.9 | 0.93 | 3.65 |

*The amount of $MgCl_2$ was calculated based on the Mg concentration found.

This experiment shows that citric acid can be precipitated from a magnesium chloride solution.

EXAMPLE 4: PREPARATION OF SUCCINIC ACID

Magnesium hydroxide (99 g) was added to a solution of 200 g succinic acid in 888 g water at room temperature and heated up to complete dissolution (by visual observation). An amount of 333 g aqueous solution of HCl (37 wt. % wt %) was added to the thus prepared magnesium succinate solution. The temperature of the thus obtained mixture was initially 62° C. The mixture was cooled to 20° C. and a precipitate was formed. During cooling, samples were taken of the solution and the precipitate of the mixture at 62, 52, 40, 31 and 20° C. The composition of the samples and the total amount of precipitate formed were determined.

The samples were taken only from the solution (for sampling, stirrer was stopped some few seconds, and after crystal settling, a sample was taken from the supernatant). Magnesium and succinic acid in solution were analyzed and expressed as g/g water. The amount of crystal produced was calculated as difference between the initial succinic acid mass and the mass of the succinic acid remaining in solution.

The results are shown in Table 8.

TABLE 8

| Temperature (° C.) | Succinic Acid concentration in the solution (wt. %) | Mg concentration in the solution (wt. %) | Amount of succinic acid formed (g) |
|---|---|---|---|
| 62 | 13.13 | 2.71 | 0 |
| 52 | 8.20 | 1.82 | 82 |
| 40 | 5.00 | 3.15 | 130 |
| 31 | 3.40 | 3.20 | 153 |
| 20 | 2.10 | 3.19 | 171 |

Furthermore, the amount of succinic acid in the 182 g precipitate formed during the cooling step was determined, which was 94.4% corresponding to 172 g. The rest of the precipitate consisted mainly of water (4.4%) and magnesium chloride. These findings correspond to a total recovery of succinic acid of over 85%.

This example shows that during precipitation, the majority of succinic acid precipitates, while substantially all magnesium ions remain in solution. It can be concluded that acidulation with HCl and subsequent crystallization results in a very efficient separation of succinic acid from the magnesium succinate solution.

EXAMPLE 5: PRECIPITATION AFTER CONCENTRATING

To the magnesium succinate solution as prepared in Example 4 an aqueous solution of HCl (37 wt. %) was added, thereby obtaining 500 g solution comprising 2.1 wt. % succinic acid and 12.6 wt. % $MgCl_2$ (corresponding to a $MgCl_2$ concentration of 14.8 g per 100 g water). The solution was then concentrated by water evaporation, thereby obtaining 199 g solution comprising 5.3 wt. % succinic acid and 31.7 wt. % magnesium chloride (corresponding to a $MgCl_2$ concentration of 50.2 g per 100 g water, which is close to the saturation point of $MgCl_2$ in water, which is 55 g/100 g water at 20° C.). The initial and final values of the solution are summarized in Table 9.

TABLE 9

|  | concentration (wt %) | | $MgCl2$ ratio to water (mass based) |
| --- | --- | --- | --- |
|  | mass (g) | $MgCl_2$ | Succinic | g/100 gH2O |
| initial | 500 | 12.6 | 2.1 | 14.8 |
| final | 199 | 31.7 | 5.3 | 50.2 |

The solution was then cooled from 115° C. to 20° C. Precipitation started at 82° C. and continued until 20° C. The precipitate was separated from the solution by filtration using a standard gravity filter. The composition of the precipitate and the solution is show in Table 10.

TABLE 10

|  | Content succinic (%) | $Cl^-$ (wt. %) | $Mg^{+2}$ (wt. %) | water (wt. %) |
| --- | --- | --- | --- | --- |
| Solution | 0.22 | 25.0 | 6.6 | — |

The succinic acid present in the filtrate was determined using high-performance liquid chromatography (HPLC) and was 0.22 wt. %. Assuming that all succinic acid not present in the filtrate would be present in the precipitate, the value of 0.22 wt. % would correspond to a succinic acid yield in the precipitate of over 90%.

The invention claimed is:

1. A method for the recovery of a carboxylic acid, comprising:
    providing an aqueous solution or suspension of magnesium carboxylate, wherein the carboxylic acid corresponding with the carboxylate has a solubility in water at 20° C. of 80 g/100 g water or less;
    obtaining solid magnesium carboxylate from the solution or suspension, dissolving the solid magnesium carboxylate in water to create an aqueous solution, and acidifying the obtained aqueous solution of magnesium carboxylate with a solution of hydrogen chloride (HCl), thereby obtaining a solution comprising carboxylic acid and magnesium chloride ($MgCl_2$);
    optionally a concentration step, wherein the solution comprising carboxylic acid and $MgCl_2$ is concentrated; and,
    precipitating carboxylic acid from the solution comprising carboxylic acid and $MgCl_2$, thereby obtaining a carboxylic acid precipitate and a $MgCl_2$ solution.

2. The method according to claim 1, wherein the carboxylic acid has a solubility in water at 20° C. that is lower than that of $MgCl_2$.

3. The method according to claim 1, wherein the carboxylic acid has a solubility in water of less than 30 g/100 g water.

4. The method of claim 1, wherein the carboxylic acid is selected from the group consisting of adipic acid, itaconic acid, 2,5-furandicarboxylic acid, fumaric acid, oxalic acid, maleic acid, glutaric acid, malonic acid, and fatty acids having more than 10 carbon atoms.

5. The method according to claim 1, wherein:
    the aqueous solution or aqueous suspension comprises at least 10 wt. % magnesium carboxylate, based on the total weight of the solution or suspension; and,
    the solution comprising the carboxylic acid and $MgCl_2$ comprises at least 5 wt. % of magnesium chloride based on the total weight of the solution comprising carboxylic acid.

6. The method according to claim 1, wherein magnesium carboxylate is provided in dissolved form, as part of an aqueous solution obtained in a fermentation process or as part of an aqueous suspension obtained in a fermentation process.

7. The method according to claim 6, wherein the magnesium carboxylate is provided in dissolved form as part of an aqueous suspension obtained in a fermentation process by neutralization of carboxylic acid with a magnesium base and wherein, in the aqueous suspension, at least 95 wt. % of the magnesium carboxylate is in dissolved form.

8. The method according to claim 7, wherein the aqueous suspension consists of dissolved magnesium carboxylate and insoluble biomass.

9. The method according to claim 1, wherein the aqueous solution or suspension of magnesium carboxylate provided in the providing step is concentrated by evaporation to obtain the solid magnesium carboxylate.

10. The method according to claim 9, wherein, in the obtaining solid magnesium carboxylate from the solution or suspension step, the concentrated solution or suspension of magnesium carboxylate is subjected to solid-liquid separation.

11. The method according to claim 1, wherein acidifying the magnesium carboxylate and precipitating the carboxylic acid thus formed are conducted in one step.

12. The method according to claim 1, wherein the $MgCl_2$ solution or concentrated $MgCl_2$ solution is subjected to a second precipitation step to recover at least part of the carboxylic acid remaining in the $MgCl_2$ solution obtained in the first precipitation step.

13. The method according to claim 12, wherein the second precipitation is conducted by cooling and/or concentrating the $MgCl_2$ solution.

14. The method according to claim 12, wherein additional $MgCl_2$ is added to the $MgCl_2$ solution prior to the second precipitation.

15. The method according to claim 1, wherein the solution comprising the carboxylic acid and $MgCl_2$ is concentrated to a carboxylic acid concentration that is equal or up to 10 g/L lower than the saturation point of the carboxylic acid.

16. The method according to claim 1, wherein the solution comprising the carboxylic acid and $MgCl_2$ is concentrated to a carboxylic acid concentration that is equal or up to 5 g/L lower than the saturation point of the carboxylic acid.

17. The method according to claim 1, further comprising:
    subjecting the $MgCl_2$ solution to a thermal decomposition step at temperatures of at least 300° C., thereby decomposing the $MgCl_2$ to magnesium oxide (MgO) and HCl;
    dissolving the HCl formed in the thermal decomposition step in water, thereby obtaining a HCl solution; and
    bringing the MgO in contact with water, thereby obtaining $Mg(OH)_2$, which $Mg(OH)_2$ is optionally recycled for use in a fermentation process.

18. The method according to claim 17, wherein thermal decomposition is conducted using a spray roaster.

19. The method according to claim 17, wherein the thermal decomposition is conducted at a pressure in a range of from 0.1-10 bar.

20. The method according to claim 17, wherein the thermal decomposition is conducted at a temperature ranging from 300-450° C.

21. The method according to claim 17, wherein $Mg(OH)_2$ is converted to $MgCO_3$, which is then used as a neutralizing agent in a fermentation process.

22. The method according to claim 17, wherein thermal decomposition is conducted by spraying the $MgCl_2$ solution into contact with a stream of hot gas.

23. The method according to claim 1, further comprising subjecting the $MgCl_2$ solution to a thermal decomposition step at temperatures of at least 300° C., thereby decomposing the $MgCl_2$ to magnesium oxide (MgO) and HCl.

24. The method according to claim 23, wherein the HCl obtained in the thermal decomposition step is used in the acidifying step either as HCl gas or as an aqueous HCl solution, the solution being obtained through dissolving the HCl formed in the thermal decomposition step in water.

25. The method according to claim 23, wherein at least a part of the MgO is recycled for use in a fermentation process.

26. The method according to claim 23, further comprising bringing at least a part of the MgO in contact with water, thereby obtaining $Mg(OH)_2$.

27. The method according to claim 26, wherein at least a part of the $Mg(OH)_2$ is recycled for use in a fermentation process.

28. The method according to claim 23, further comprising
bringing at least a part of the MgO in contact with water, thereby obtaining $Mg(OH)_2$; and,
converting at least a part of the $Mg(OH)_2$ to $MgCO_3$, which is then used as a neutralizing agent in a fermentation process.

29. The method according to claim 6, wherein the aqueous solution obtained in the fermentation process or suspension obtained in the fermentation process further comprises the carboxylic acid.

30. The method according to claim 6, wherein the magnesium carboxylate is provided in dissolved form as part of an aqueous suspension obtained in a fermentation process by neutralization of carboxylic acid with a magnesium base, and wherein the aqueous suspension comprises up to 10 wt. % solids.

* * * * *